United States Patent [19]

Black et al.

[11] Patent Number: 4,656,187

[45] Date of Patent: Apr. 7, 1987

[54] TREATMENT OF MAMMARY CANCER

[75] Inventors: Larry J. Black; James A. Clemens, both of Indianapolis, Ind.

[73] Assignee: Eli Lilly and Company, Indianapolis, Ind.

[21] Appl. No.: 556,875

[22] Filed: Dec. 1, 1983

Related U.S. Application Data

[63] Continuation of Ser. No. 289,360, Aug. 3, 1981, abandoned.

[51] Int. Cl.$^4$ .................... A61K 31/40; A61K 31/135
[52] U.S. Cl. ...................................... 514/422; 514/648
[58] Field of Search ................ 424/330, 274; 514/648, 514/422

[56] References Cited

U.S. PATENT DOCUMENTS

| | | | |
|---|---|---|---|
| 2,914,563 | 11/1959 | Allen et al. | 260/570 |
| 3,272,841 | 9/1966 | DeWald | 260/326.5 |
| 3,274,213 | 9/1966 | Lednicer | 260/326.5 |
| 3,875,242 | 4/1975 | Lednicer | 260/613 |
| 4,133,814 | 1/1979 | Jones et al. | 260/326.55 |
| 4,230,862 | 10/1980 | Suarez et al. | 546/237 |

FOREIGN PATENT DOCUMENTS 1013907  12/1965  United Kingdom .

OTHER PUBLICATIONS

Faye et al., Biochem. And Biophys. Res. Comm. 93, 1225–31 (1980).
Sutherland et al., *Nature* 288, 273–75 (1980).
U.S. Application Ser. No. 246,335, Jones, Eli Lilly and Co. filed Apr. 3, 1981.

*Primary Examiner*—Jerome D. Goldberg
*Attorney, Agent, or Firm*—Bruce J. Barclay; Joseph A. Jones; Leroy Whitaker

[57] ABSTRACT

Mammary cancers are inhibited by administration of a combination of two drugs. The first compound is 6-hydroxy-2-(4-hydroxyphenyl)-3-[4-(2-pyrrolidinoethoxy)benzoyl]benzo[b]thiophene, and the second compound is tamoxifen.

2 Claims, 5 Drawing Figures

TREATMENT OF MAMMARY CANCER

This application is a continuation of application Ser. No. 289,360, filed Aug. 3, 1981, now abandoned.

BACKGROUND OF THE INVENTION

1. Field of the Invention

This invention relates to the field of biochemistry, and provides a method of treating mammary cancer with certain antiestrogenic agents.

Estrogen is transported by the bloodstream and passively enters cells. However, only certain tissues exhibit responses to the hormone and are accordingly called estrogen target tissues. These target tissues are characterized by the presence of specific estrogen receptors. The interaction of the estrogen with estrogen receptors in the cytoplasm of target cells is an early event in a complex series of events which result in an estrogenic response. The uterus, vagina and breast are considered the primary target tissue for estrogen. They are rich in estrogen receptors and exhibit dramatic growth under the influence of estradiol. The uterotropic response of laboratory animals is a convenient, reproducible model for the evaluation of antiestrogenic and estrogenic activity, as well as for the study of interactions with estrogen receptors.

A relationship has been established between estrogen sensitivity or dependency, and the occurrence of estrogen receptors in mammary cancers. The neutralization of estrogen influence on those tissues is expected to benefit patients with such a cancer by inhibiting the growth of it, and even by causing the regression of the cancer or by preventing recurrence of it.

Antiestrogens antagonize the action of estrogens, such as estradiol, in animals and display clinical efficacy in about half of the mammary cancers which contain estrogen receptors. They interact with estrogen receptors, and elicit partial estrogenic responses. Their estrogenic response is measured and described by their partial agonist (uterotropic) properties. Known antiestrogens display, in widely varying degrees, some agonist characteristics: that is, the administration of one of them to a normal animal produces some uterotropic response, as though a weak estrogen had been administered; this effect is termed the agonist effect. Such compounds also exhibit an estrogen antagonist effect: that is, administration of one of them to an estrogen-treated animal will cause a reduction in the uterotropic response caused by the estrogen.

It has long been known that estrogen target tissues have many receptor sites which specifically bind estradiol. It has more recently been proposed that such tissues also contain another receptor site, which does not appear to bind estradiol, but which does bind some known antiestrogens. See Faye et al., *Biochem. and Biophys. Res. Comm.* 93, 1225–31 (1980), and Sutherland et al., *Nature* 288, 273–75 (1980).

This invention makes use of a combination of two antiestrogens which have quite different partial agonist/antagonist properties.

2. State of the Art

At least one drug is now sold as an antiestrogen for palliative cancer therapy; it is tamoxifen, 1-(4-β-dimethylaminoethoxyphenyl)-1,2-diphenylbut-1-ene, British Pat. No. 1,013,907.

Antiestrogens which have been clinically tested in cases of advanced mammary cancer include trioxifene mesylate, 2-[4-(2-pyrrolidinoethoxy)benzoyl]-1-(4-methoxyphenyl)-3,4-dihydronaphthalene, methanesulfonic acid salt, which is described in U.S. Pat. No. 4,230,862, of Suarez and Jones, clomiphene, 2-[4-(2-chloro-1,2-diphenylvinyl)phenoxy]triethylamine, U.S. Pat. No. 2,914,563, of Allen et al., and nafoxidine, 6-methoxy-2-phenyl-1-[4-(2-pyrrolidinoethoxy)phenyl]-3,4-dihydronaphthalene.

The benzothiophenes of Jones and Suarez, U.S. Pat. No. 4,133,814, are also known antiestrogens. Tests of one of their compounds, 6-hydroxy-2-(4-hydroxyphenyl)-3-[4-(2-pyrrolidinoethoxy)benzoyl]benzo[b]thiophene, LY117018, have been published by Black and Goode, *Life Sciences* 26, 1453–58 (1980). The same article also discussed similar tests of tamoxifen and trioxifene, giving their partial agonist/antagonist properties.

Another pertinent document on antiestrogens is U.S. patent application Ser. No. 246,335 of Jones, which teaches 6-hydroxy-2-(4-hydroxyphenyl)-3-[4-(2-piperidinoethoxy)benzoyl]benzo[b]thiophene and some derivatives thereof, which compound is described as a particularly effective antiestrogen.

SUMMARY OF THE INVENTION

The present invention provides a method of inhibiting the growth of estrogen-dependent mammary cancers comprising administering to a patient in need of such treatment about 20 mg./kg./day of a first compound which is 6-hydroxy-2-(4-hydroxyphenyl)-3-[4-(2-pyrrolidinoethoxy)benzoyl]benzo[b]thiophene, and about 5 mg./kg./day of a second compound which is tamoxifen. The present also provides a pharmaceutical combination comprising about four parts by weight of a first compound which is 6-hydroxy-2-(4-hydroxyphenyl)-3-[4-(2-pyrrolidinoethoxy)benzoyl]benzo[b]thiophene, and about one part by weight of a second compound which is tamoxifen.

DESCRIPTION OF THE DRAWINGS

The drawings are graphs showing the uterotropic effect of various treatments with compounds used in the invention, alone or in combination, and are presented to illustrate the above-described properties of preferred first and second compounds. All of the data reported in the graphs were obtained in tests such as were described by Black and Goode, cited above, and represent the means of at least 6 animals per data point.

DESCRIPTION OF THE PREFERRED EMBODIMENTS

This invention is defined as a method of inhibiting mammary cancers, by which it is meant that the method of this invention slows down the rate of growth of such cancers. It will be understood that in many cases the reduction in growth rate amounts to a reversal of the growth, so that the cancer will reduce in size and may even disappear. If the method is applied to a patient in whom such a cancer has been removed or regressed, or who is believed for some reason to have a risk of mammary cancer, the growth inhibition effect is observed as delayed onset of a mammary cancer, or in the form of complete prevention of such a cancer or a recurrence of it.

The mammary cancers which are affected by the method of this invention are those which are at least partially estrogen-dependent or estrogen-sensitive. It is believed that about one-third of all mammary cancers are so affected by estrogen.

The patients in need of the treatment of this invention are those which have active estrogendependent or sensitive mammary cancers, or which are believed to be at risk of such cancers. Use of the method in human patients is preferred, but the method may also be applied, if desired, to other mammalian species.

The compounds used in the present method are generally described here in terms of their uterotropic effect in female laboratory animals, compared to the effect of estradiol as a standard. See Black and Goode, cited above, for a discussion of a test method which is typical and accepted by those skilled in the testing of antiestrogens. The method is carried out by administering the compound to be tested, subcutaneously, and sacrificing the animals at the end of the treatment and removing and weighing the uteri. When the estrogen antagonist effect is to be determined, the test compound is administered together with the estrogen for 3 days.

First Compounds

Figure 1:
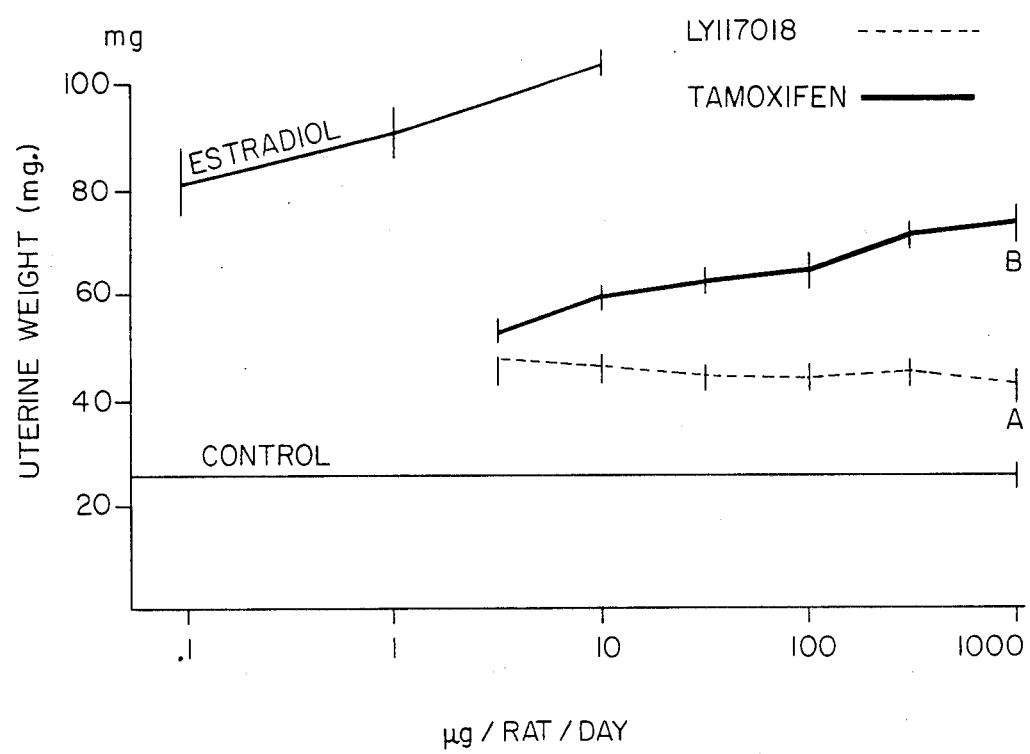
FIG. 1 shows the uterotropic effect of estradiol at three doses in immature rats, compared to the effects of a preferred first compound and a preferred second compound. The first compound, Curve A, is LY117018, and the second compound, Curve B, is tamoxifen.

The first compounds of this invention are described as having non-dose-related uterotropic effect. By this phrase it is meant that compounds which are suitable for use as first compounds are those which produce a partial uterotropic effect at a low dose which does not increase when the dose is increased, when measured in an immature rat assay such as was described by Black and Goode. The maximum uterotropic effect of a first compound is small, compared to the maximum effect of estradiol. Such compounds also have a uterotropic effect which is substantially independent of the dose at which the compound is administered over a wide range of dosages, such as from about 1 to about 1000 micrograms per rat per day in the immature rat assay. FIG. 1, Curve A, shows the uterotropic effect of a preferred first compound, compared to the effect of estradiol. The small, non-dose-related nature of the uterotropic effect is clearly seen.

First compounds are further described as those which can substantially or completely antagonize, block or regress the uterotropic effect of estradiol. Thus, such compounds are those which can reduce the estradiol effect to a value equal to or less than the uterotropic effect of the compound alone, whether the compound is administered before, after, or at the same time that the estradiol is administered. If administered before the estradiol, the first compound can block the estradiol effect from occurring; if administered after estradiol is administered, it can regress the estradiol effect; and if administered at the same time, it antagonizes the estradiol effect.

Figure 2:
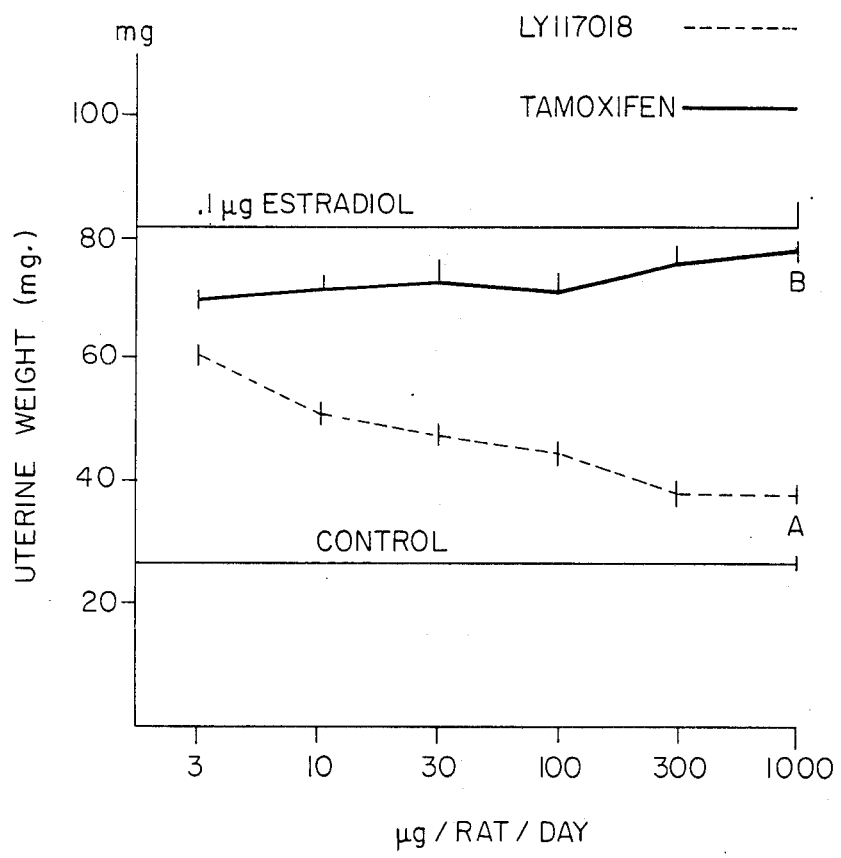
FIG. 2 shows the estradiol antagonist effects of LY117018 and tamoxifen at several doses in immature rats. Curve A shows the effect of LY117018 combined with 0.1 microgram of estradiol, and Curve B shows the effect of tamoxifen when administered in the same way.
Figure 3:
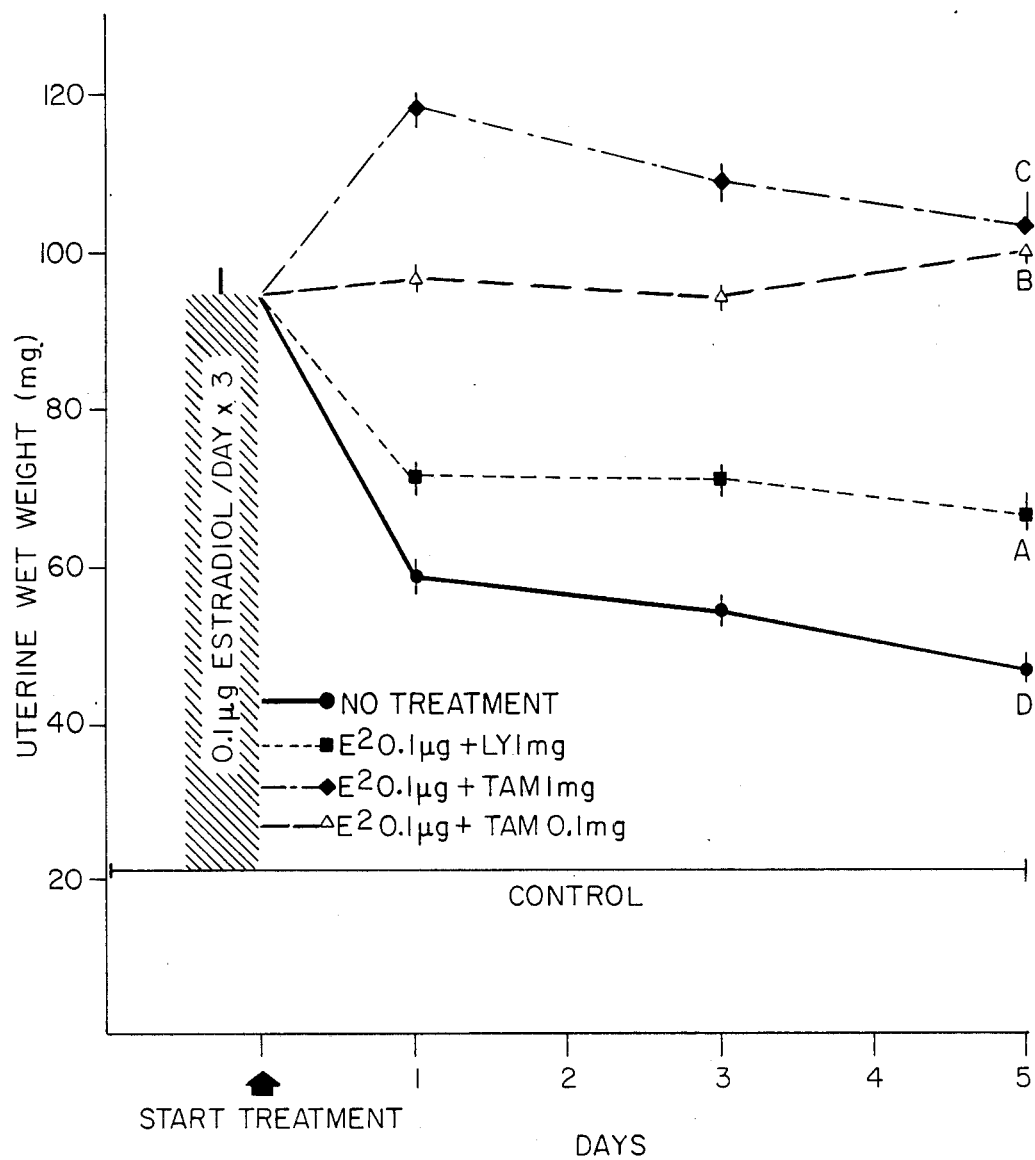
FIG. 3 shows regression tests, in which 0.1 microgram of estradiol was administered to ovariectomized rats for 3 days. Then the rats were treated with estradiol combined with LY117018, Curve A, or tamoxifen at one of two rates, Curves B and C, to determine whether the estradiol effect was regressed. Curve D shows the effect of stopping all treatment after the third day.

FIG. 2, Curve A shows the estradiol antagonistic effect of a preferred first compound when administered to immature rats at various doses, together with 0.1 microgram of estradiol. Curve A of FIG. 3 shows the regressive effect of a preferred first compound, and FIG. 4, Curve B shows the ability of the same compound to block the uterotropic effect when it is administered before estradiol treatment.

Figure 5:
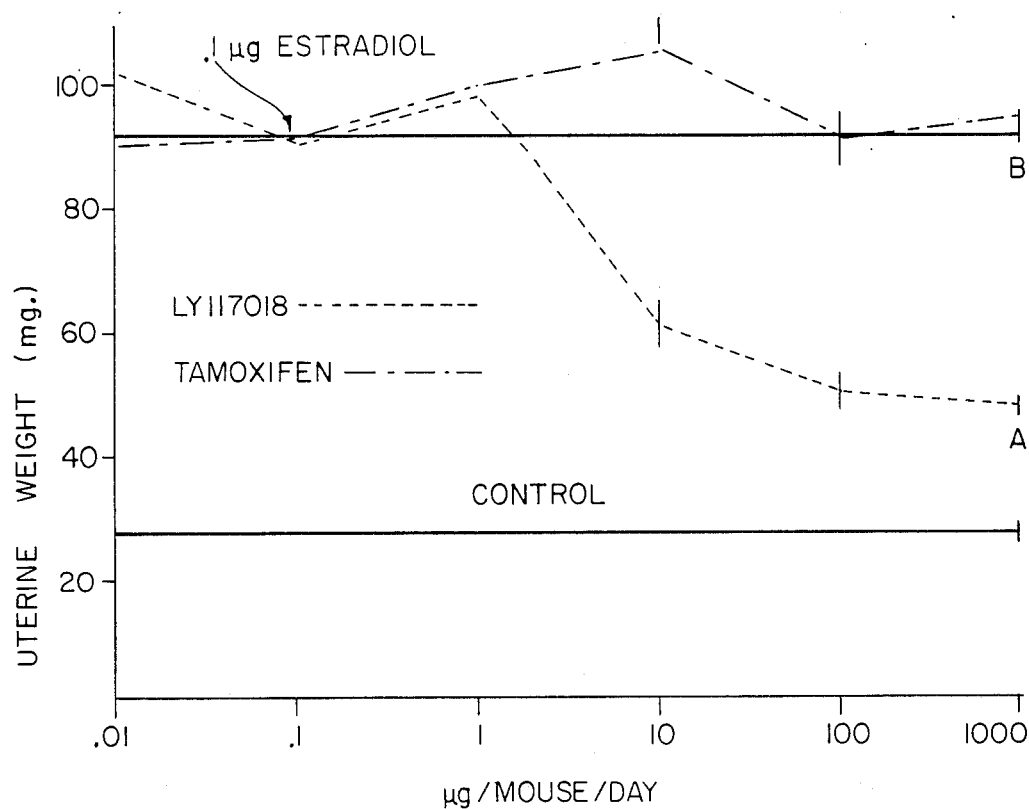
FIG. 5 shows estradiol antagonist tests similar to those of FIG. 2, but in adult ovariectomized mice. Curve A shows the effect of LY117018 combined with estradiol, and curve B shows the effect of tamoxifen with estradiol.

First compounds can antagonize the estradiol effect in adult ovariectomized mice, as demonstrated by curve A of FIG. 5.

Figure 4:
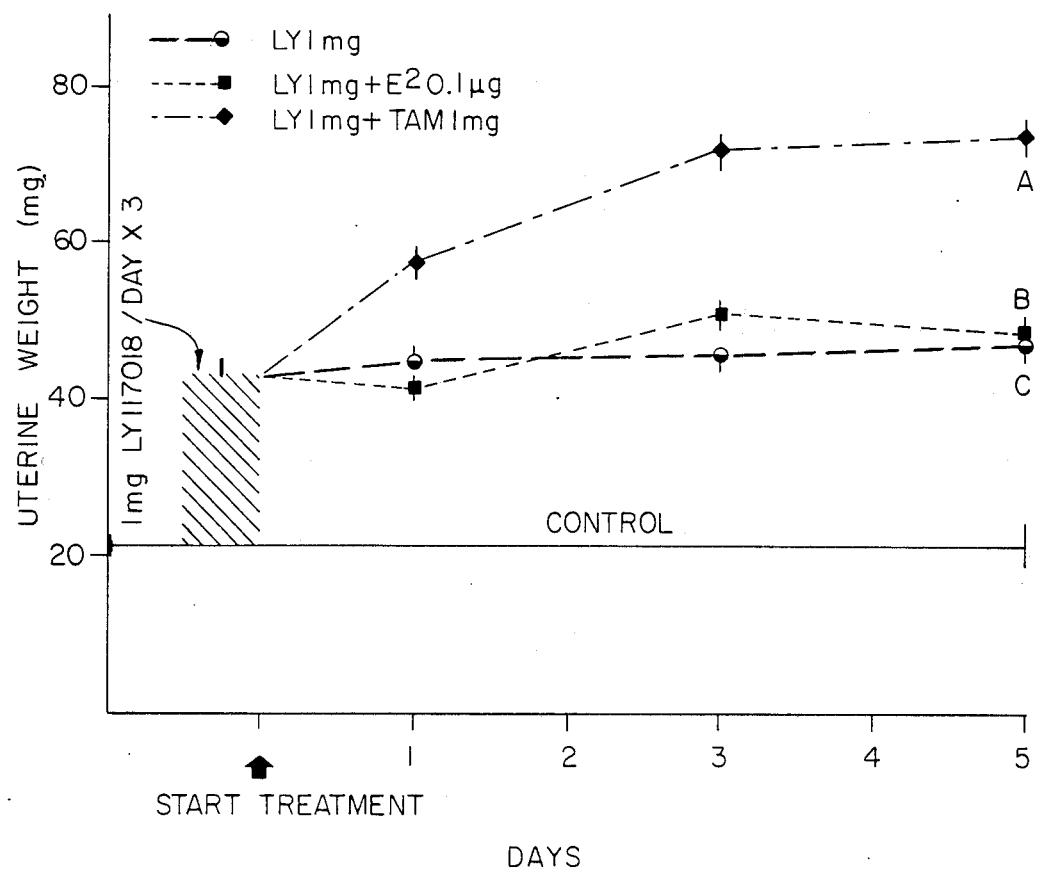
FIG. 4 shows blocking tests, carried out by administering a preferred first compound, LY117018, to ovariectomized rats for 3 days, and then administering LY117018 combined with tamoxifen, curve A, or with estradiol, curve B. Curve C shows the effect of continuing to administer LY117018 alone.

Finally, a first compound cannot antagonize or block the uterotropic effect of a second compound to the same high degree that it can antagonize or block the effect of estradiol. The determination of that property of the first compounds is performed by testing the second compound in the immature rat assay alone, and testing it again in combination with the candidate first compound. FIG. 4, curve A, shows the inability of a preferred first compound to block the uterotropic effect of a preferred second compound.

The first compound employed in the invention is 6-hydroxy-2-(4-hydroxyphenyl)-3-[4-(2-pyrrolidinoethoxy)benzoyl]benzo[b]thiophene.

The compounds can be obtained by processes known to the art. U.S. Pat. No. 4,133,814, of Jones and Suarez, illustrates the synthesis of the pyrrolidino compound. The piperidino compound may also be made by the same processes. A newer and more effective process for preparing the compounds proceeds by way of a methyl-protected starting compound, which synthesis is illustrated by the following two examples.

Preparation 1

6-methoxy-2-(4-methoxyphenyl)benzo[b]thiophene

A 100 g. portion of 3-methoxybenzenethiol and 39.1 g. of potassium hydroxide dissolved in 300 ml. of water were added to 750 ml. of denatured ethanol, and the flask was put in a cooling bath. A total of 164 g. of α-bromo-4-methoxyacetophenone was then added in small portions, and the mixture was stirred for 10 minutes in the cooling bath after the addition was complete and then for 3 hours at ambient temperature. The solvent was then evaporated off in vacuum, and 200 ml. of water was added. The mixture was extracted with ethyl acetate, and the organic layer was washed twice with water, twice with aqueous sodium bicarbonate solution, and twice with aqueous sodium chloride solution. The organic layer was then dried over magnesium sulfate, filtered and evaporated under vacuum to obtain 202 g. of crude α-(3-methoxyphenylthio)-4-methoxyacetophenone, which was recrystallized from methanol and washed with hexane to obtain 158 g. of purified product, m.p. 53° C.

A 124 g. portion of the above intermediate was added in small portions to 930 g. of polyphosphoric acid at 85° C. The temperature rose to 95° C. during the addition, and the mixture was stirred at 90° C. for 30 minutes after the addition was complete, and was then stirred an additional 45 minutes while it cooled without external heating. One liter of crushed ice was then added to the mixture, and an external ice bath was applied to control the temperature while the ice melted and diluted the acid. Five hundred ml. of additional water was added, and the light pink precipitate was filtered off and washed, first with water and then with methanol. The solids were dried under vacuum at 40° C. to obtain 119 g. of crude 6-methoxy-2-(4-methoxyphenyl)-benzo[b]-thiophene. The crude product was slurried in hot methanol, filtered, and washed with cold methanol, and the solids were recrystallized from 4 liters of ethyl acetate, filtered, washed with hexane and dried to obtain 68 g. of the desired intermediate product, m.p. 187–190.5° C.

EXAMPLE 1

6-hydroxy-2-(4-hydroxyphenyl)-3-[4-(2-piperidinoethoxy)benzoyl]benzo[b]thiophene, hydrochloride Under a nitrogen blanket, a mixture of 3 g. of 4-(2-piperidinoethoxy)benzoic acid, hydrochloride, 2 drops of dimethylformamide, 2.5 ml. of thionyl chloride and 40 ml. of chlorobenzene was heated at 70°–75° C. for about one hour. The excess thionyl chloride and 15–20 ml. of solvent were then distilled off. The remaining suspension was cooled to ambient temperature, and to it were added 100 ml. of dichloromethane, 2.7 g. of 6-methoxy-2-(4-methoxyphenyl)benzo[b]thiophene and 10 g. of aluminum chloride. The solution was stirred for about one hour, 7.5 ml. of ethanethiol was added, and the mixture was stirred for 45 minutes more. Then 40 ml. of tetrahydrofuran was added, followed by 15 ml. of 20% hydrochloric acid, with an exotherm to reflux. Fifty ml. of water and 25 ml. of saturated aqueous sodium chloride were added. The mixture was stirred and allowed to cool to ambient temperature. The precipitate was collected by filtration and washed successively with 30 ml. of water, 40 ml. of 25% aqueous tetrahydrofuran, and 35 ml. of water. The solids were then dried at 40° C. under vacuum to obtain 5.05 g. of product, which was identified by its nmr spectrum, using a 90 mHz instrument and deuterochloroform. $\delta 1.7$ (6H, m, $N(CH_2CH_2)_2CH_2$); 2.6–3.1 (2H, m, $NCH_2$); 3.5–4.1 (4H, m, $NCH_2$); 4.4 (2H, m, $OCH_2$); 6.6–7.4 (9H, m, aromatic); 7.7(2H, d, aromatic o to CO); 9.8 (2H, m, OH).

EXAMPLE 2

6-hydroxy-2-(4-hydroxyphenyl)-3-[4-(2-pyrrolidinoethoxy)benzoyl]benzo[b]thiophene, hydrochloride The acid chloride was made from 2.85 g. of 4-(2-pyrrolidinoethoxy)benzoic acid, hydrochloride, as described in Example 1. The excess thionyl chloride and most of the solvent were distilled off, and to the residue at ambient temperature were added 80 ml. of dichloromethane, 2.7 g. of 6-methoxy-2-(4-methoxyphenyl)benzo[b]thiophene and 10 g. of aluminum chloride. The mixture was stirred for 45 minutes, 7.5 ml. of ethanethiol was added, and the mixture was stirred for 45 minutes more. To it were then added 5 ml. of methanol, 35 ml. of tetrahydrofuran, 20 ml. of 20% hydrochloric acid, 40 ml. of water and 50 ml. of diethyl ether. A precipitate formed, and was collected by filtration, washed with water and diethyl ether, and dried under vacuum at 80° C. to obtain 4.36 g. of the desired product in crude form.

One gram of the product was dissolved in 10 ml. of hot methanol and filtered, and the filtrate was concentrated to 5 ml. Ten ml. of diethyl ether was slowly added to it with cooling. The resulting crystals were collected by filtration, washed with diethyl ether and dried at 100° C. under vacuum to obtain 0.9 g. of purified product, m.p. 226°–227° C., which was identified by 90 mHz nmr analysis in DMSO-$d_6$: $\delta 1.1$ (t, 2H, $OCH_2CH_2$); 1.9 (m, 4H, $N(CH_2CH_2)_2$); 3.0–3.7 (m, 8H, $CH_2N(CH_2CH_2)_2$ and $OCH_2CH_2$); 4.3–4.5 (m, 2H, $OCH_2CH_2$); 6.6–7.8 (m, 11H, aromatic); 9.87–9.88 (m, 2H, OH).

When it is desired to prepare a compound in ether form, the ether is prepared by placing the $R^3$ moiety on one or both of the hydroxy groups in a manner commonly used for the preparation of ethers. For example, the $R^3$ group may be added by reaction with an appropriate diazo compound, such as diazomethane, phenyldiazomethane or trimethylsilyldiazomethane (see Hashimoto et al., Tet. Let., 4619–22 (1980).) Such reactions are effectively carried out in solvents including esters such as ethyl acetate, halogenated solvents including dichloromethane and chloroform, and ethers including diethyl ether and tetrahydrofuran. Methanol or boron trifluoride is used as a catalyst, and the process is usually carried out at low temperatures from about −45° C. to about 0° C. Alternatively, alkylations may be carried out with the assistance of reagents such as trimethyloxosulfonium hydroxide, trimethylsulfonium hydroxide and trimethylselenonium hydroxide (all of which provide methyl groups), as taught by Yamauchi, Tet. Let., 1787–90 (1979). Alkylations with these reagents are carried out in solvents which are conducive to $S_N2$ displacements such as dimethylsulfoxide, dimethylformamide, hexamethylphosphoramide, acetone, acetonitrile and the like, usually at elevated temperatures from about 40° C. to about the reflux temperature of the mixture.

Such alkylations may neatly be used to provide a mono-ether product, by partially hydrolyzing the intermediate product, so that one of the protecting groups is left in place, alkylating, and completing the hydrolysis to remove the remaining protecting group.

It is preferable, however, to prepare monoethers by using an ultimate starting compound in the mono-ether form, and using the ether group as a protecting group through the synthesis, protecting the other hydroxy with an acyl or sulfonyl group.

When a compound is desired wherein one or both hydroxy groups are substituted with —COR, it may often be most convenient to prepare the compound using a protecting group other than the desired —COR group, hydrolyze off the protecting group, and re-acylate one or both of the hydroxy groups at the end of the synthesis. Such acylations are carried out as is known in the art. A particularly preferred condition for final acylations is to use tetrahydrofuran as the solvent and potassium carbonate as the acid scavenger for acylating agents such as acetic anhydride, benzyl chloride, ethyl chloroformate and the like. Another preferred reaction condition for very reactive acylating reagents such as trifluoroacetic anhydride is to use an equivalent of the corresponding acid (trifluoroacetic acid in the above instance) in tetrahydrofuran at about ambient temperature, and to add the acylating agent as the last addition to the reaction mixture.

The compounds are very often administered in form of acid addition salts. The salts are conveniently formed, as is usual in organic chemistry, by reacting the compound of this invention with a suitable acid, such as have been described above. The salts are quickly formed in high yields at moderate temperatures, and often are prepared by merely isolating the compound from a suitable acidic wash as the final step of the synthesis. The salt-forming acid is dissolved in an appropriate organic solvent, or aqueous organic solvent, such as an alkanol, ketone or ester. On the other hand, if the compound of this invention is desired in the free base form, it is isolated from a basic final wash step, according to the usual practice. A preferred technique for preparing hydrochlorides is to dissolve the free base in a suitable solvent and dry the solution thoroughly, as over molecular sieves, before bubbling hydrogen chloride gas through it.

Second Compounds

Effective second compounds have a relatively pronounced uterotropic effect. Thus, when such compounds are tested in an immature rat assay, a strong uterotropic response is obtained at high doses.

Further, the uterotropic effect of a second compound is positively dose-related. As the dose of the compound is increased in the immature rat assay, for example over the range from 1 to 1000 micrograms per rat, the extent of the uterotropic response will increase in proportion to dose, and at its maximum is similar to the effect of a physiological dose of estradiol, which is 0.1 microgram for immature rats. Curve B of FIG. 1 shows the strong, dose-related uterotropic effect of a preferred second compound.

The estrogen antagonist activity of a second compound is biphasic. In other words, the antagonistic effect increases up to a certain dosage, and decreases with higher doses, as is clearly shown for a preferred second compound by Curve B of FIG. 2.

A second compound will not regress the effect of estradiol when the estradiol effect is established by prior treatment. Thus, if immature rats are treated daily with estradiol for three days, and concomitant estradiol and second compound treatments are then begun, the initial uterotropic effect of the estradiol is not reduced. Curves B and C of FIG. 3 illustrate the result for a preferred second compound.

Finally, a second compound is recognized by its inability to antagonize the estradiol effect in adult ovariectomized mice, as demonstrated by Curve B of FIG. 5.

The second compound of the invention is tamoxifen, the properties and preparation of which are set out in British Pat. No. 1,013,907, of ICI Laboratories.

The doses of the first and second compounds are adequately large to bring about, in combination, the desired inhibition of growth of the cancer. Both of the compounds are antiestrogens, and thus are known to be effective, at least to a degree, in inhibiting the growth of mammary cancers when administered alone to a patient. The benefit of the method of this invention, however, lies in its ability to produce more inhibition of a mammary cancer than could be hoped for from the known activity of the compounds when administered independently. In general, each of the compounds is administered in a dose from about 0.5 to about 20 mg./kg/day.

The compounds which make up the combination treatment of this invention are effective when administered either orally or parenterally. Thus, the combination may be administered as a single formulation or separately, in the form of oral preparations such as tablets, capsules, suspensions or the like, as injectable solutions or suspensions, or as preparations for rectal absorption such as suppositories or gels. The formulations are conventional.

The synergistic effect of the treatment method of this invention has been determined in intact animals in a test which has been accepted by the art as predictive of success in treating mammary cancers.

Mammary tumors were induced in adult female virgin rats by a 20-mg. oral dose of 7,12-dimethylbenzanthracene. Within about 6 weeks, visible and palpable tumors were present in the mammary tissue of the rats, and the rats were allocated into treatment and control groups in such a way that each group contained animals having approximately the same size and number of tumors. The size of the tumors was estimated by measuring their cross-sectional area.

The compounds administered were 6-hydroxy-2-(4-hydroxyphenyl)-3-[4-(2-pyrrolidinoethoxy)benzoyl]-benzo[b]thiophene, the first compound, called compound A hereafter, and tamoxifen, the second compound, called compound B hereafter. The doses were 20 mg./kg./day orally of compound A, and 5 mg./kg./day orally of compound B, and the treatment was continued for 8 weeks. The control animals were handled daily and given an oral dose of 0.5 ml. of corn oil, as a blank.

The table below shows the total areas of all of the tumors of each of the individual test animals. The four treatment groups, in order, are the control animals, those treated with compound A, those treated with compound B, and those treated with the combination of compounds A and B.

TABLE 1

| Animal | Controls | | Compound A | | Compound B | | Combination | |
|---|---|---|---|---|---|---|---|---|
| | Before | After | Before | After | Before | After | Before | After |
| 1 | 30 | 352 | 24 | 150 | 28 | 16 | 80 | 454 |
| 2 | 92 | 1344 | 20 | 112 | 25 | 196 | 30 | 88 |
| 3 | 40 | 626 | 110 | 2295 | 24 | 1112 | 20 | 36 |
| 4 | 0 | died | 49 | 16 | 80 | 336 | 16 | 0 |
| 5 | 42 | 796 | 64 | 651 | 16 | 0 | 25 | 0 |
| 6 | | | 20 | 0 | 32 | 112 | 42 | 0 |
| Mean | 42 | 780 | 48 | 537 | 34 | 295 | 36 | 96 |

The results of the above experiment clearly show the remarkable effect of the combination treatment. No less than 3 of the combination-treated animals experienced a total regression of their tumors, compared with only one animal in each of the groups treated with the compounds individually. Further, it is notable that two of the other three combination-treated animals experienced only a very modest growth of their tumors during the treatment, and that even the worst of the combination-treated animals had less tumor growth than did the average of the control animals.

We claim:

1. A method of inhibiting the growth of estrogen-dependent mammary cancers comprising administering to a patient in need of such treatment about 20 mg./kg./day of a first compound which is 6-hydroxy-2-(4-hydroxyphenyl)-3-[4-(2-pyrrolidinoethoxy)benzoyl]-benzo[b]thiophene, and about 5 mg./kg./day of a second compound which is tamoxifen.

2. A pharmaceutical combination comprising about four parts by weight of a first compound which is 6-hydroxy-2-(4-hydroxyphenyl)-3-[4-(2-pyrrolidinoethoxy)benzoyl]benzo[b]thiophene, and about one part by weight of a second compound which is tamoxifen.

* * * * *